(12) United States Patent
Harada et al.

(10) Patent No.: US 8,969,324 B2
(45) Date of Patent: Mar. 3, 2015

(54) PHARMACEUTICAL COMPOSITION COMPRISING 11-DEOXY-PROSTAGLANDIN COMPOUND AND METHOD FOR STABILIZING THE COMPOUND

(75) Inventors: Yasuhiro Harada, Tokyo (JP); Junichi Kawasaki, Tokyo (JP); Yoshie Nishimura, Tokyo (JP); Ryuji Ueno, Montgomery, MD (US)

(73) Assignees: R-Tech Ueno, Ltd., Tokyo (JP); Sucampo AG, Zug (CH)

( * ) Notice: Subject to any disclaimer, the term of this patent is extended or adjusted under 35 U.S.C. 154(b) by 478 days.

(21) Appl. No.: 12/174,230

(22) Filed: Jul. 16, 2008

(65) Prior Publication Data

US 2009/0022787 A1    Jan. 22, 2009

Related U.S. Application Data

(60) Provisional application No. 60/929,948, filed on Jul. 19, 2007.

(51) Int. Cl.
*A01N 57/00*  (2006.01)
*A61K 9/48*  (2006.01)
*A61K 31/5575*  (2006.01)

(52) U.S. Cl.
CPC .......... *A61K 9/4858* (2013.01); *A61K 31/5575* (2013.01)
USPC ........................................................ 514/81

(58) Field of Classification Search
None
See application file for complete search history.

(56) References Cited

U.S. PATENT DOCUMENTS

| | | | |
|---|---|---|---|
| 3,271,434 A * | 9/1966 | Baenitz | 554/173 |
| 4,310,543 A | 1/1982 | Gallo-Torres et al. | |
| 4,431,833 A * | 2/1984 | Lodhi et al. | 560/2 |
| 4,871,772 A * | 10/1989 | Miwa et al. | 514/573 |
| 5,166,174 A * | 11/1992 | Ueno et al. | 514/530 |
| 6,183,466 B1 * | 2/2001 | Wong et al. | 604/892.1 |
| 6,583,174 B1 * | 6/2003 | Ueno et al. | 514/456 |
| 2006/0194880 A1 * | 8/2006 | Ueno | 514/573 |

FOREIGN PATENT DOCUMENTS

| | | | |
|---|---|---|---|
| JP | 53-50141 A * | 5/1978 | |
| NZ | 570191 | 9/2010 | |
| WO | 2006/080549 A2 | 8/2006 | |
| WO | WO 2006080549 A2 * | 8/2006 | |
| WO | 2006/093348 A2 | 9/2006 | |
| WO | 2007/086536 A2 | 8/2007 | |

OTHER PUBLICATIONS

Beck et al.; Antihypertensive activity of 16,16-dimethyl-oxa-alkyl-prostgalandins of the PGA2, PGE2 and trans-Delta 2-11-deoxy-PGE1 series: Structure Activity relationships; Prostaglandins, Butterworth, Stonham, MA, US, vol. 20, No. 1, Jul. 1, 1980; pp. 159-169.
Oral Anti-Ulcer Activity of a Synthetic Prostaglandin Analogue (9-Oxoprostanoic Acid: AY-22,469); Experientia, Birkhaeuser Verlag. Basel, CH, vol. 29, No. 8, Aug. 15, 1973, p. 993.
Russian Office Action for Application No. 2010105847 issued Jan. 24, 2013.
Russian Office Action dated Jun. 13, 2012 issued in a corresponding Russian Application No. 2010105847.
Chueshov et al., "Manufacturing Process of Medicaments" in 2 volumes—Kharkov: Editorial House NFAU MTK-Kniga—2000-vol. 2-p. 396.
Summons to Attend Oral Proceedings Pursuant to Rule 115(1) EPC issued on Apr. 16, 2014, in the corresponding European Patent Application No. 08778342.9, 7 pages.
Database WPI, Week 197824, Thomson Scientific, London, GB; AN 1978-43080A, 1 p. (1978).
English translation of JP 53-50141, publication date May 8, 1978, 7 pages.

* cited by examiner

*Primary Examiner* — Susan Tran
(74) *Attorney, Agent, or Firm* — Sughrue Mion, PLLC

(57) ABSTRACT

Provided is a pharmaceutical composition comprising a 11-deoxy-prostaglandin compound represented by formula (I):

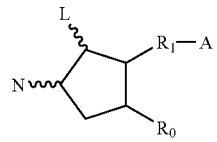

and a fatty acid ester. By mixing the compound of formula (I) and a fatty acid ester, the compound of formula (I) will be stabilized.

26 Claims, No Drawings

PHARMACEUTICAL COMPOSITION COMPRISING 11-DEOXY-PROSTAGLANDIN COMPOUND AND METHOD FOR STABILIZING THE COMPOUND

CROSS REFERENCE TO RELATED APPLICATION

This application claims the benefit of U.S. Provisional Application No. 60/929,948 filed Jul. 19, 2007.

TECHNICAL FIELD

The present invention relates to a pharmaceutical composition comprising specific 11-deoxy-prostaglandin compound, method for stabilizing said therapeutically effective 11-deoxy-prostaglandin compound and a soft gelatin capsule formulation comprising the 11-deoxy-prostaglandin compound as an active ingredient.

BACKGROUND ART

Prostaglandin has a prostanoic acid structure indicated by the formula:

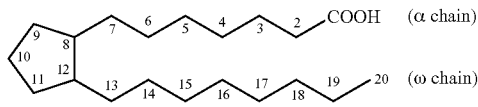 [SMILES: CCCCCCCCC1CCCC1CCCCCCC(=O)O]

and there are many prostaglandins expressing a variety of therapeutic effects.

11-deoxy-prostaglandin compounds such as 11-deoxy-15-keto-16,16-difluoro prostaglandin $E_1$:

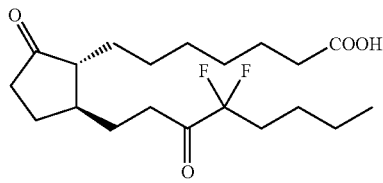 [SMILES: CCCCC(F)(F)C(=O)CC[C@H]1CCC(=O)[C@@H]1CCCCCCC(=O)O]

are useful for the improvement of central nerves system dysfunction as well as peripheral circular dysfunction (WO2006/093348 and WO2006/080549, the cited references are herein incorporated by reference).

SUMMARY OF THE INVENTION

An object of the present invention is to provide a pharmaceutical composition comprising a specific 11-deoxy-prostaglandin compound in a stabilized form. Another object of the present invention is to provide a method for stabilizing the specific 11-deoxy-prostaglandin compound. A further object of the present invention is to provide a soft gelatin capsule.

In the first aspect of the present invention, a pharmaceutical composition comprising a 11-deoxy-prostaglandin compound represented by the formula (I):

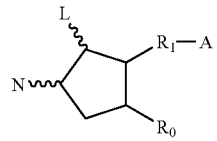

wherein L and N are hydrogen, hydroxy, halogen, lower alkyl, hydroxy(lower)alkyl, lower alkanoyloxy or oxo, wherein the five-membered ring may optionally have at least one double bond;

A is —$CH_3$, —$CH_2OH$, —$COCH_2OH$, —COOH or a functional derivative thereof;

$R_1$ is a saturated or unsaturated bivalent lower or medium aliphatic hydrocarbon, which is unsubstituted or substituted with halogen, lower alkyl, hydroxy, oxo, aryl or heterocyclic group, and at least one carbon atom in the aliphatic hydrocarbon is optionally substituted by oxygen, nitrogen or sulfur; and $R_0$ is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group, and at least one carbon atom in the aliphatic hydrocarbon is optionally substituted by oxygen, nitrogen or sulfur, and a fatty acid ester.

In the second aspect of the present application, a method for stabilizing the 11-deoxy-prostaglandin compound defined as above, which comprises mixing the 11-deoxy-prostaglandin compound and a fatty acid ester is provided.

In the third aspect of the present application, a soft gelatin capsule formulation, which comprises a soft gelatin capsule shell comprising a polyol and/or sugar alcohol as a plasticizer, and a pharmaceutical composition comprising the above defined 11-deoxy-prostaglandin compound and a pharmaceutically acceptable vehicle, wherein the composition is incorporated in the gelatin capsule shell.

A more preferred 11-deoxy-prostaglandin compound used in the present invention is represented by the formula (II):

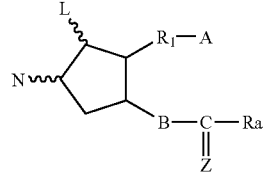

wherein B is single bond, —$CH_2$—$CH_2$—, —CH=CH—, —C≡C—, —$CH_2$—$CH_2$—$CH_2$—, —CH=CH—$CH_2$—, —$CH_2$—CH=CH—, —C≡C—$CH_2$— or —$CH_2$—C≡C—;

Z is

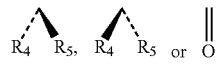

wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group, and at least one carbon atom in the aliphatic hydrocarbon is optionally substituted by oxygen, nitrogen or sulfur; and L, N, A and $R_1$ are the same as defined above.

A group of particularly preferable 11-deoxy-prostaglandin compounds among the above-described compounds is represented by the formula (III):

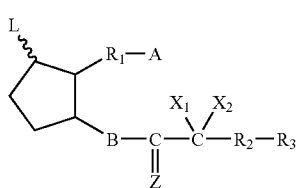

(III)

wherein $X_1$ and $X_2$ are hydrogen, lower alkyl, or halogen; $R_2$ is a single bond or lower alkylene;

$R_3$ is lower alkyl, lower alkoxy, lower alkanoyloxy, cyclo(lower)alkyl, cyclo(lower)alkyloxy, aryl, aryloxy, heterocyclic group or heterocyclic-oxy group, and at least one carbon atom in the aliphatic hydrocarbon is optionally substituted by oxygen, nitrogen or sulfur; and L, A, B, $R_1$ and Z are the same as defined above.

PREFERRED EMBODIMENT

In the above formula, the term "unsaturated" in the definitions for $R_1$ and Ra represents an aliphatic hydrocarbon that include one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 6 to 10 carbon atoms for $R_1$ and 1 to 10, especially 1 to 8 carbon atoms for $R_a$.

The term "halogen" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, sec-butyl, t-butyl, pentyl and hexyl.

The term "lower alkoxy" refers to a group of lower alkyl-O—, wherein lower alkyl is defined as above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is defined as above.

The term "aryl" may include unsubstituted or substituted aromatic hydrocarbon rings (preferably monocyclic groups), for example, phenyl, naphthyl, tolyl and xylyl. Examples of the substituents are halogen atom and halogen substituted lower alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, sec-butyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)

alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, sec-butyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, sec-butyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower)alkyl ester such as hydroxyethyl ester; lower alkoxy(lower)alkyl esters such as methoxymethyl ester and 1-methoxyethyl ester; and optionally substituted aryl esters such as, for example, phenyl ester, tosyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A mean a group represented by the formula —CONR'R", wherein each of R' and R" is hydrogen atom, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonyl-amide and tolylsulfonylamide.

Preferred examples of L include hydroxy and oxo which provide a 5-membered ring structure of, so called, especially PGF or PGE type.

Preferred examples of A are —COOH, its pharmaceutically acceptable salt, ester and amide thereof.

Preferred example of B is —CH$_2$—CH$_2$—, which provide the structure of so-called, 13,14-dihydro type compound.

Preferred example of X$_1$ and X$_2$ is hydrogen, or that at least one of them is halogen, more preferably, both of them are halogen, especially, fluorine that provides a structure of, so called 16,16-difluoro type compound.

Preferred R$_1$ is a hydrocarbon containing 1-10 carbon atoms, preferably, 6-8 carbon atoms. Further, at least one carbon atom in the aliphatic hydrocarbon is optionally substituted by oxygen, nitrogen or sulfur.

Examples of R$_1$ include, for example, the following groups:
—CH$_2$—CH$_2$—CH$_2$—CH$_2$—CH$_2$—CH$_2$—,
—CH$_2$—CH=CH—CH$_2$—CH$_2$—CH$_2$—,
—CH$_2$—CH$_2$—CH$_2$—CH$_2$—CH=CH—,
—CH$_2$—C≡C—CH$_2$—CH$_2$—CH$_2$—,
—CH$_2$—CH$_2$—CH$_2$—CH$_2$—CH(CH$_3$)—CH$_2$—,
—CH$_2$—CH$_2$—CH$_2$—CH$_2$—O—CH$_2$—,
—CH$_2$—CH=CH—CH$_2$—O—CH$_2$—,
—CH$_2$—C≡C—CH$_2$—O—CH$_2$—,
—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—,
—CH$_2$—CH$_2$—CH$_2$—CH$_2$—CH$_2$—CH=CH—,
—CH$_2$—C≡C—CH$_2$—CH$_2$—CH$_2$—CH$_2$—,
—CH$_2$—CH$_2$—CH$_2$—CH$_2$—CH$_2$—CH(CH$_3$)—CH$_2$—,
—CH$_2$—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—CH$_2$—,
—CH$_2$—CH$_2$—CH$_2$—CH$_2$—CH$_2$—CH$_2$—CH=CH—,
—CH$_2$—C≡C—CH$_2$—CH$_2$—CH$_2$—CH$_2$—CH$_2$—, and
—CH$_2$—CH$_2$—CH$_2$—CH$_2$—CH$_2$—CH$_2$—CH(CH$_3$)—CH$_2$—

Preferred Ra is a hydrocarbon containing 1-10 carbon atoms, more preferably 1-8 carbon atoms and especially 5-7 carbon atoms. The hydrocarbon of Ra may additionally have one or two side chains each having one carbon atom.

Preferred R$_2$ is single bond.

Preferred R$_3$ is lower alkyl and more preferably, alkyl having 4-6 carbon atoms. The lower alkyl of R$_3$ may additionally have one or two side chains each having one carbon atom.

The typical examples of the present compounds are 11-deoxy-13,14-dihydro-16,16-difluoro-PGE or PGF compound, 11-deoxy-13,14-dihydro-15-keto-16,16-difluoro-PGE or PGF compound, 2-decarboxy-2-(2-carboxyethyl)-11-deoxy-13,14-dihydro-15-keto-16,16-difluoro-PGE or PGF compound, or 11-deoxy-13,14-dihydro-15-keto-16,16-difluoro-20-ethyl-PGE or PGF compound and its derivative or analogue.

The preferred examples of the compounds may include 11-deoxy-13,14-dihydro-15-keto-16,16-difluoro-PGE$_1$, 11-deoxy-13,14-dihydro-16,16-difluoro-PGE$_1$, 11-deoxy-13,14-dihydro-15-keto-16,16-difluoro-PGE$_1$ isopropyl ester, 2-decarboxy-2-(2-carboxyethyl)-11-deoxy-13,14-dihydro-15-keto-16,16-difluoro-PGE$_1$ isopropyl ester, 2-decarboxy-2-(2-carboxyethyl)-11-deoxy-13,14-dihydro-15-keto-16,16-difluoro-PGE$_1$, 11-deoxy-13,14-dihydro-15-keto-16,16-difluoro-20-methyl-PGE$_1$ isopropyl ester, 11-deoxy-13,14-dihydro-15-keto-16,16-difluoro-20-methyl-PGE$_1$, 11-deoxy-13,14-dihydro-15-keto-16,16-difluoro-20-ethyl-PGE$_1$, 11-deoxy-13,14-dihydro-15-keto-16,16-difluoro-PGE$_1$ methyl ester, 11-deoxy-13,14-dihydro-15-keto-16,16-difluoro-20-ethyl-PGE$_1$ isopropyl ester or 11-deoxy-13,14-dihydro-15-keto-16,16-difluoro-20-ethyl-PGF$_{1\alpha}$ isopropyl ester.

In the present invention, the 11-deoxy-prostaglandin compound of formula (I) covers any isomers of formula (I) including the individual tautomeric isomers, the mixture thereof, or optical isomers, the mixture thereof, a racemic mixture, and other steric isomers.

Some of the compounds used in the present invention may be prepared by the method disclosed in WO2006/080549 and WO2006/093348 and the references cited therein (these cited references are herein incorporated by reference).

The pharmaceutical composition of the present invention comprises the above described 11-deoxy-prostaglandin compound and a fatty acid ester.

Examples of the fatty acid esters used in the present invention may include fatty acid esters obtained from a fatty acid and an alcohol, for example, saturated or unsaturated glycerides which may have a branched chain. Preferred fatty acid esters may include a medium or higher chain fatty acid having at least C6, preferably C6-24 carbon atoms, for example caproic acid (C6), caprylic acid (C8), capric acid (C10), lauric acid (C12), myristic acid (C14), palmitic acid (C16), palmitoleic acid (C16), stearic acid (C18), oleic acid (C18), linoleic acid (C18), linolenic acid (C18), ricinolic acid (C18) and arachic acid (C20). Preferred alcohols which consists the fatty acid ester may comprise C1-6 monovalent alcohol and polyols such as glycerine, polyethyleneglycol and propyleneglycol.

Preferred fatty acid esters may include a glyceride of a saturated or unsaturated fatty acid which may have a branched chain, a glycerine fatty acid ester and a propyleneglycol fatty acid ester. Two or more glycerides may be used as a mixture.

Examples of the mixture of glycerides are mixture of caprylic acid triglyceride and capric acid triglyceride, vegetable oils such as castor oil, corn oil, olive oil, sesame oil, rape oil, salad oil, cottonseed oil, camellia oil, peanut oil, palm oil and sunflower oil.

A fatty acid ester derived from a fatty acid and a monovalent alcohol is also preferably used. The fatty acid ester may preferably be an ester of a C8-20 fatty acid and a C2-3 monovalent alcohol, such as isopropyl miristate, isopropyl palmitate, ethyl linoleate and ethyl oleate.

The composition of the present invention may be prepared by dissolving or dispersing the above described 11-deoxy-prostaglandin compound in the fatty acid ester. When it is difficult to dissolve the 11-deoxy-prostaglandin compound directly in the fatty acid ester, each of them may be dissolved in a solvent in which both of them are soluble respectively, and then the solutions may be combined.

The amount of the fatty acid ester in the composition relative to the amount of the 11-deoxy-prostaglandin compound is not limited as long as the 11-deoxy-prostaglandin compound is stable in the composition. In general, the amount of the fatty acid ester per one part of the 11-deoxy-prostaglandin compound may be 1-5,000,000, preferably, 5-1,000,000 and most preferably, 10-500,000 parts by weight.

The pharmaceutical composition of the present invention may further comprise physiologically acceptable additives which do not provide adverse effect to the stability of the compound of formula (I). The additives which may be employed in the present invention include, but not limited to, excipients, diluents, fillers, solvents, lubricants, adjuvants, binders, disintegrants, coatings, capuslating agents, ointment bases, suppository bases, aerozoles, emulsifiers, dispersing agents, suspensions, viscosity increasing agents, isotonic agents, buffers, analgesic agents, preservatives, anti-oxidants, corrigents, flavors, colorants, and functional agents such as cyclodextrin, biologically degradable polymers. The additives may be selected from those described in any of general textbooks in the pharmaceutical field. The composition of the present invention may further comprise one or more other pharmaceutically active ingredient.

According to the present invention, the dosage form of the composition is not specifically limited and is preferably in the form suitable for oral administration. More preferably, the composition of the present invention is in the form of capsule such as hard capsule or soft capsule.

Sugar alcohol solution derived from corn starch and glycerine have been known that they can be used as plasticizer for manufacturing soft-gelatin capsules. Sugar alcohol solution derived from corn starch and glycerine have also been known to deteriorate the stability of 11-deoxy-prostaglandin compound recited in the instant application when admixed directly with the compound and therefore, the art would expect that sugar alcohols or polyols are not useful as plasticizer for manufacturing soft gelatin capsule to incorporate the 11-deoxy-prostaglandin compound of the invention as an active ingredient. The inventor have surprisingly found that soft gelatin capsule shell manufactured from gelatin and a sugar alcohol or a polyol as a plasticizer will not deteriorate the stability of 11-deoxy-prostaglandin compound of the invention when the composition comprising the 11-deoxy-prostaglandin compound and a fatty acid ester is incorporated in the soft gelatin capsule shell.

According to the present invention, the composition which is filled in the soft-gelatin capsule shell may be obtained by dissolving or dispersing the above-described 11-deoxy-prostaglandin compound in a pharmaceutically acceptable vehicle which is liquid at the room temperature. When it is difficult to dissolve the 11-deoxy-prostaglandin compound directly in the vehicle, each of them may be dissolved in a solvent in which both of them are soluble respectively, and then the solutions may be combined.

The pharmaceutically acceptable vehicle may be any of those employed for the manufacture of medicaments as long as they do not deteriorate the stability of the active ingredient, 11-deoxy-prostaglandin compound.

Preferred embodiment of the composition to be filled in the soft gelatin capsule shell is a composition comprising the 11-deoxy-prostaglandin compound and a fatty acid ester.

The amount of the vehicle in the composition relative to the amount of the 11-deoxy-prostaglandin compound is not limited as long as the 11-deoxy-prostaglandin compound is stable in the final formulation. In general, the amount of the vehicle per one part of the 11-deoxy-prostaglandin compound may be 1-5,000,000, preferably, 5-1,000,000 and most preferably, 10-500,000 parts by weight.

According to the present invention, the pharmaceutical composition to be filled in the soft gelatin capsule may further comprise oil solvent other than the fatty acid ester such as mineral oil, liquid paraffin, and tocopherol.

Polyols used in the present invention are alcohols having two or three hydroxy groups. Preferred examples of polyols may include glycerine, polyethyleneglycol and propyleneglycol.

Sugar alcohol plasticizer used in the present invention is an alcohol obtained by hydrogen reduction of the aldehyde group of a saccharide. Examples may comprise sorbitol, mannitol, maltitol, lactitol, palatinit, xylitol and erithyritol; and sugar alcohol solution derived from corn starch, i.e. a mixture of sorbitol, sorbitan, mannitol and hydrogenated starch hydrolysate, hydrogenated maltose starch syrup, i.e. a mixture of maltitol, sorbitol and oligosaccharide alcohol.

Preferred sugar alcohols may include sorbitol, sorbitan, maltitol, sugar alcohol solution derived from corn starch and hydrogenated maltose starch syrup. Especially, sugar alcohol solution derived from corn starch and available on market under the name "Anidrisorb" or "Polysorb" is preferably used.

According to the invention, the amount of the sugar alcohol used for preparing the shell of the soft gelatin capsule is not specifically limited as long as the physical properties of the resulting capsule is not deteriorated. In general, the amount of sugar alcohol plasticizer is 20-60 parts by weight, preferably, 30-50 parts by weight per 100 parts by weight of gelatin.

The soft gelatin capsule formulation comprising the 11-deoxy-prostaglandin compound as an active ingredient may be manufactured by filling a composition comprising the 11-deoxy-prostaglandin compound and a pharmaceutically acceptable vehicle in soft gelatin capsule shell manufactured from gelatin and a plasticizer, polyol and/or sugar alcohol. Thus obtained soft gelatin capsule formulation can keep the 11-deoxy-prostaglandin compound stably for long term. Manufacture of soft gelatin capsule shell as well as filling the composition into the shell may be conducted according to a conventional manner.

The present invention will be explained in more detail by means of the following examples, which are illustrated by way of example only and never intended to limit the scope of the present invention.

EXAMPLE 1

Compound 1

11-deoxy-13,14-dihydro-15-keto-16,16-difluoro PGE1

Compound 1 was dissolved in a vehicle shown in table 1 below to give 250 μg/g solution. Then, the solution was put in a hard grass container and heated at 55° C. The precise amount of Compound 1 in the solution was determined by means of HPLC (day 0). The container was kept at 55° C. for 10 days and after that the precise amount of the compound 1 was determined by means of HPLC (day 10).

The determination of the amount of the compound was carried out as follows. About 0.2 g of the sample was mixed with exactly 2 mL of internal standard solution and then with a dissolving agent shown in Table 1 to give 5 mL of sample solution. About 5 mg of the reference standard compound 1 was weighted precisely and added with acetonitrile to give exactly 50 ml solution. Exactly 1 ml of the solution was obtained and added with exactly 4 mL of the internal standard solution, and then added with the dissolving agent to give 10 mL of reference solution.

The fluorescent labeling agent was added to the respective solution, stirred and stood at room temperature for more than 30 minutes. After that, 2% acetic acid in acetonitrile was added to the solution, stirred and reacted at room temperature for more 30 minutes to give the sample and standard solutions. Then, the respective solution in an amount that theoretically gives 3.6 ng of compound 1 was loaded on the column and analyzed under the condition as follows:

HPLC Analysis Condition:
  Column: 5 mm×25 cm stainless steel column packed with octadecylsilane treated silica gel for HPLC (5 μm)
  Mobile phase: mixture of acetonitrile (HPLC grade) and perchlorate buffer
  Temperature: 35° C.
  Detector: spectrophotofluorometer
Results are shown in Table 1

TABLE 1

Stability of Compound 1: stored at 55° C.

| | vehicle | dissolving agent | day 0[1] | day 10[1] |
|---|---|---|---|---|
| 1 | medium chain fatty acid triglyceride[2] | acetonitrile | 94.1% | 97.0% |
| 2 | corn oil | ethyl acetate | 93.1% | 94.8% |
| 3 | soy oil | acetonitrile | 98.2% | 94.6% |
| 4 | glycerine fatty acid ester[3] | acetonitrile | 93.3% | 96.4% |
| 5 | propyleneglycol fatty acid ester[4] | acetonitrile | 93.9% | 92.1% |
| 6 | isopropyl palmitate | acetonitrile | 93.9% | 96.7% |

[1]percentage based on the theoretical amount (250 μg/g)
[2]Miglyol 812N, constituting fatty acids: caproic acid (C6) NMT 2.0%, caprylic acid (C8) 50.0-80.0%, capric acid (C10) 20.0-50.0%, lauric acid (C12 NMT) 3.0%, and myristic acid (C14) NMT 1.0% (NF/EP).
[3]Inwitor 742, total monoglycerides are 44-55%
[4]Rikemal PO-100V, proplylene glycol monooleate, Riken Vitamin Co., Ltd.

COMPARATIVE EXAMPLE 1

According to the same manner as described in Example 1, stability of the compound 1 in various vehicles was measured. Results are shown in Table 2.

TABLE 2

Stability of Compound 1: stored at 55° C.

| | vehicle | dissolving agent | day 0[1] | day 10[1] |
|---|---|---|---|---|
| 1 | - (compound 1 only) | acetonitrile | 95.4% | 82.8% |
| 2 | concentrated glycerin | methanol | 20.9% | 20.0% |
| 3 | hydrogenated maltose starch syrup | acetonitrile/water (1:1) | 5.1% | 3.5% |
| 4 | sugar alcohol solution derived from corn starch | methanol | 3.8% | 5.6% |
| 5 | Macrogol 400 (polyethyleneglycol) | acetonitrile | 92.2% | 80.7% |
| 6 | polysorbate 80 | acetonitrile | 92.1% | 64.5% |
| 7 | oleic acid | methanol | 61.9% | 51.6% |

[1]percentage based on the theoretical amount (250 μg/g)

According to the results of Example 1 and Comparative Example 1, the stability of compound 1 was significantly improved by admixing the same with a fatty acid ester such as glyceride. In contrast, the stability of the compound 1 was poor in polyol such as glycerine, sugar, sugar alcohol, polyethylene glycol, polysorbate 80, and fatty acid.

PREPARATION EXAMPLE

Soft Gelatin Capsule

Compound 1: 11-deoxy-13,14-dihydro-15-keto-16,16-difluoro PGE1 was used.

FORMULATION EXAMPLE

Sugar alcohol solution derived from corn starch 60 parts by weight was added in an appropriate amount of water, stirred and heated. Then, gelatin 100 parts by weight was added thereto to give gelatin solution. Compound 1 was dissolved in medium chain fatty acid triglyceride (USP/NF grade) to give a liquid mixture containing 120 μg/g of compound 1. The gelatin solution and the liquid mixture were loaded on a soft capsule forming and filling machine to give capsule containing the liquid mixture, and dried to give soft gelatin capsule with an appropriate hardness.

EXAMPLE 2

The soft gelatin capsules obtained in the formulation example were kept at 40° C. for 6 months or at 55° C. for one month. After that, 20 capsules were swelled with purified water and ethyl acetate (HPLC grade) 10 mL was added thereto. The capsule was then cut opened and the liquid contained therein was obtained. 1 mL of the internal standard solution per 100 μg of theoretical amount of compound 1 was added to the liquid, and ethyl acetate (HPLC grade) was added so that the theoretical concentration of compound 1 was 10 μg/mL to give a sample solution.

On the other hand, about 0.025 g of standard Compound 1 was precisely weighted and added with ethyl acetate (HPLC grade) to give exactly 100 mL solution. 2 mL of the solution was measured, exactly 5 mL of the internal standard solution was added thereto and ethyl acetate (HPLC grade) was added so that the total amount was 50 mL to give the standard compound 1 solution.

The fluorescent labeling agent was added to the sample and standard solutions, stirred and reacted at room temperature.

The respective solution in an amount that theoretically gives 3.6 ng of compound 1 was loaded on the column and analyzed under the condition as follows:

HPLC Analysis Condition:

Column: 5 mm×25 cm stainless steel column packed with octadecylsilane treated silica gel for HPLC (5 μm)

Mobile phase: mixture of acetonitrile HPLC grade: methanol HPLC grade: ammonium acetate (0.05 mol/L)

Temperature: 35° C.

Detector: spectrophotofluorometer

The amount of the compound 1 in the sample solution was determined by using a one point calibration curve. Results are shown in Tables 3 and 4 below:

TABLE 3

Stability of Compound 1: stored at 40° C.

| gelatin solution | | amounts of compound 1 on 1, 3 and 6 months (% vs day 0) | | | |
|---|---|---|---|---|---|
| gelatin | sugar alcohol solution | Initial | 1 mo | 3 mo | 6 mo |
| 100 | 60 | 100 | 99.8 | 98.0 | 98.8 |

TABLE 4

Stability of Compound 1: stored at 55° C.

| gelatin solution | | amounts of compound 1 on 1, 2 and 4 weeks (% vs day 0) | | | |
|---|---|---|---|---|---|
| gelatin | sugar alcohol solution | Initial | 1 w | 2 w | 4 w |
| 100 | 60 | 100 | 100.2 | 100.1 | 99.5 |

The sugar alcohol solution/polyol which decreased the stability of compound 1 when directly admixed with the compound will not affect the stability when used as plasticizer.

What is claimed is:

1. A pharmaceutical composition comprising a 11-deoxy-prostaglandin compound represented by formula (III):

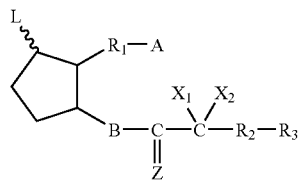

(III)

wherein L is hydrogen, hydroxy, halogen, lower alkyl, hydroxy(lower)alkyl, lower alkanoyloxy or oxo, wherein the five-membered ring may optionally have at least one double bond;

A is —$CH_3$, —$CH_2OH$, —$COCH_2OH$, —COOH or a functional derivative thereof;

B is single bond, —$CH_2$—$CH_2$—, —CH=CH—, —C≡C—, —$CH_2$—$CH_2$—$CH_2$—, —CH=CH—$CH_2$—, —$CH_2$—CH=CH—, —C≡C—$CH_2$— or —$CH_2$—C≡C—;

$R_1$ is a saturated or unsaturated bivalent lower or medium aliphatic hydrocarbon, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur;

$R_2$ is a single bond or lower alkylene;

$R_3$ is lower alkyl, lower alkoxy, lower alkanoyloxy, cyclo(lower)alkyl, cyclo(lower)alkyloxy, aryl, aryloxy, heterocyclic group or heterocyclic-oxy group, and at least one carbon atom in the aliphatic hydrocarbon is optionally substituted by oxygen, nitrogen or sulfur;

$X_1$ and $X_2$ are hydrogen, lower alkyl, or halogen; and

Z is =O, and a fatty acid ester derived from (1) a fatty acid and (2) glycerine.

2. The composition as described in claim 1, wherein said 11-deoxy-prostaglandin compound is a 11-deoxy-13,14-dihydro-prostaglandin compound.

3. The composition as described in claim 1, wherein said 11-deoxy-prostaglandin compound is a 11-deoxy-15-keto-prostaglandin compound.

4. The composition as described in claim 1, wherein said 11-deoxy-prostaglandin compound is a 11-deoxy-13,14-dihydro-15-keto-prostaglandin compound.

5. The composition as described in claim 1, wherein said 11-deoxy-prostaglandin compound is a 11-deoxy-16-mono or dihalogen-prostaglandin compound.

6. The composition as described in claim 1, wherein said 11-deoxy-prostaglandin compound is a 11-deoxy-13,14-dihydro-16-mono or dihalogen-prostaglandin compound.

7. The composition as described in claim 1, wherein said 11-deoxy-prostaglandin compound is a 11-deoxy-15-keto-16-mono or dihalogen-prostaglandin compound.

8. The composition as described in claim 1, wherein said 11-deoxy-prostaglandin compound is a 11-deoxy-13,14-dihydro-15-keto-16-mono or dihalogen-prostaglandin compound.

9. The composition as described in claim 1, wherein said 11-deoxy-prostaglandin compound is a 11-deoxy-13,14-dihydro-15-keto-16-mono or difluoro-prostaglandin compound.

10. The composition as described in claim 1, wherein said 11-deoxy-prostaglandin compound is a 11-deoxy-13,14-dihydro-15-keto-16-mono or dihalogen-prostaglandin E or F compound.

11. The composition as described in claim 1, wherein said prostaglandin compound is 11-deoxy-13,14-dihydro-15-keto-16-mono or difluoro-prostaglandin E or F compound.

12. The composition as described in claim 1, wherein said 11-deoxy-prostaglandin compound is a 11-deoxy-13,14-dihydro-15-keto-16,16-difluoro-prostaglandin $E_1$ compound.

13. The composition as described in claim 1, wherein said fatty acid ester is a glyceride of a fatty acid having 6-24 carbon atoms.

14. The composition as described in claim 1, wherein said fatty acid ester is a glyceride of a fatty acid having 6-20 carbon atoms.

15. The composition as described in claim 1, wherein said fatty acid ester is a mixture of two or more glycerides.

16. The composition as described in claim 1, wherein said fatty acid ester is mixed with an oil vehicle other than fatty acid ester.

17. The composition as described in claim 16, wherein said oil vehicle is a mineral oil.

18. The composition as described in claim 1, wherein L is oxo.

19. The composition as described in claim 1, wherein A is —COOH.

20. The composition as described in claim 1, wherein $X_1$ and $X_2$ are both halogen.

21. The composition as described in claim 20, wherein the halogen is fluorine.

22. The composition as described in claim 1, wherein $R_1$ is C6-8 aliphatic hydrocarbon.

23. The composition as described in claim 1, wherein $R_1$ is selected from the following group:

—$CH_2$—$CH_2$—$CH_2$—$CH_2$—$CH_2$—$CH_2$—,
—$CH_2$—$CH$=$CH$—$CH_2$—$CH_2$—$CH_2$—,
—$CH_2$—$CH_2$—$CH_2$—$CH_2$—$CH$=$CH$—,
—$CH_2$—$C$≡$C$—$CH_2$—$CH_2$—$CH_2$—,
—$CH_2$—$CH_2$—$CH_2$—$CH_2$—$CH(CH_3)$—$CH_2$—,
—$CH_2$—$CH_2$—$CH_2$—$CH_2$—$O$—$CH_2$—,
—$CH_2$—$CH$=$CH$—$CH_2$—$O$—$CH_2$—,
—$CH_2$—$C$≡$C$—$CH_2$—$O$—$CH_2$—,
—$CH_2$—$CH_2$—$CH_2$—$CH_2$—$CH_2$—$CH_2$—$CH_2$—,
—$CH_2$—$CH$=$CH$—$CH_2$—$CH_2$—$CH_2$—$CH_2$—,
—$CH_2$—$CH_2$—$CH_2$—$CH_2$—$CH_2$—$CH$=$CH$—,
—$CH_2$—$C$≡$C$—$CH_2$—$CH_2$—$CH_2$—$CH_2$—,
—$CH_2$—$CH_2$—$CH_2$—$CH_2$—$CH_2$—$CH(CH_3)$—$CH_2$—,
—$CH_2$—$CH_2$—$CH_2$—$CH_2$—$CH_2$—$CH_2$—$CH_2$—$CH_2$—,
—$CH_2$—$CH$=$CH$—$CH_2$—$CH_2$—$CH_2$—$CH_2$—$CH_2$—,
—$CH_2$—$CH_2$—$CH_2$—$CH_2$—$CH_2$—$CH_2$—$CH$=$CH$—,
—$CH_2$—$C$≡$C$—$CH_2$—$CH_2$—$CH_2$—$CH_2$—$CH_2$—, and
—$CH_2$—$CH_2$—$CH_2$—$CH_2$—$CH_2$—$CH_2$—$CH(CH_3)$—$CH_2$—.

24. The composition as described in claim 1, wherein $R_1$ is —$CH_2$—$CH_2$—$CH_2$—$CH_2$—$CH_2$—$CH_2$—.

25. The composition as described in claim 1, which is in a dosage form suitable for oral administration.

26. The composition as described in claim 1, which is formulated as a capsule.

* * * * *